(12) United States Patent
Griffiths (10) Patent No.: US 10,441,480 B2
(45) Date of Patent: *Oct. 15, 2019

(54) ABSORBENT GARMENT

(71) Applicant: Knix Wear Inc., Toronto (CA)

(72) Inventor: Joanna Griffiths, Toronto (CA)

(73) Assignee: Knix Wear Inc., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/833,248

(22) Filed: Dec. 6, 2017

(65) Prior Publication Data

US 2018/0092787 A1    Apr. 5, 2018

Related U.S. Application Data

(63) Continuation of application No. 14/888,435, filed as application No. PCT/CA2014/000389 on May 2, 2014.

(Continued)

(51) Int. Cl.
*A61F 13/494*    (2006.01)
*A61F 13/496*    (2006.01)
(Continued)

(52) U.S. Cl.
CPC .. *A61F 13/49406* (2013.01); *A61F 13/15268* (2013.01); *A61F 13/496* (2013.01); *A61F 13/49017* (2013.01); *A61F 13/532* (2013.01); *A61F 13/8405* (2013.01); *A61L 15/46* (2013.01); *A61F 2013/15276* (2013.01);
(Continued)

(58) Field of Classification Search
CPC .... A61F 2013/51165; A61F 2013/4966; A61F 13/49017; A61F 13/49406; A61F 13/49446; A61F 13/49453; A61F 13/496; A61F 13/72; A61F 2013/49088;
(Continued)

(56) References Cited

U.S. PATENT DOCUMENTS 3,608,551 A    9/1971  Saburo
4,044,769 A *  8/1977  Papajohn ................ A61F 13/72
                                              604/385.19
(Continued)

FOREIGN PATENT DOCUMENTS

CA    2126280        12/1994
CA    2126281 A1     12/1994
(Continued)

OTHER PUBLICATIONS

International Search Report for PCT/CA2014/000389 dated Jul. 25, 2014.

*Primary Examiner* — Catharine L Anderson
(74) *Attorney, Agent, or Firm* — DASCENZO Intellectual Property Law, P.C.

(57) ABSTRACT

An undergarment includes a body portion having an upper edge defining a waistband, two leg openings and a crotch region between the leg openings; an absorbent pad on the inside of the body portion within at least the crotch region, the absorbent pad having an inner region and a peripheral region; and elastic bonding film bonded to each of the two leg openings and overlying respective portions of the peripheral region of the absorbent pad thereby to seamlessly bond the absorbent pad with the body portion.

25 Claims, 6 Drawing Sheets

Related U.S. Application Data (60) Provisional application No. 61/819,527, filed on May 3, 2013.

(51) Int. Cl.
*A61F 13/15* (2006.01)
*A61L 15/46* (2006.01)
*A61F 13/49* (2006.01)
*A61F 13/532* (2006.01)
*A61F 13/84* (2006.01)

(52) U.S. Cl.
CPC . *A61F 2013/8414* (2013.01); *A61L 2300/104* (2013.01); *A61L 2300/404* (2013.01)

(58) Field of Classification Search
CPC .... A61F 2013/49095; A61F 2013/4948; A61F 13/15268; A61F 2013/15276
See application file for complete search history.

(56) References Cited

U.S. PATENT DOCUMENTS

| | | | | |
|---|---|---|---|---|
| 4,560,381 A * | 12/1985 | Southwell | ............ | A61F 13/505 2/406 |
| 4,781,962 A * | 11/1988 | Zamarripa | ......... | A61F 13/5123 428/138 |
| 5,151,092 A * | 9/1992 | Buell | ............... | A61F 13/15593 604/358 |
| 5,167,897 A * | 12/1992 | Weber | ............... | A61F 13/15593 264/101 |
| 5,217,782 A * | 6/1993 | Moretz | ................. | A41B 9/004 428/91 |
| 5,308,346 A * | 5/1994 | Sneller | .................... | A61F 13/15 604/385.25 |
| 5,342,338 A * | 8/1994 | Roe | ...................... | A61F 13/511 604/358 |
| 5,360,420 A * | 11/1994 | Cook | ................ | A61F 13/15203 604/368 |
| 5,368,910 A * | 11/1994 | Langdon | ............... | A61F 13/512 428/131 |
| 5,449,352 A * | 9/1995 | Nishino | ............ | A61F 13/15731 604/358 |
| 5,500,270 A * | 3/1996 | Langdon | ............ | A61F 13/512 428/116 |
| 5,507,895 A * | 4/1996 | Suekane | ............ | A61F 13/15739 156/204 |
| 5,518,801 A * | 5/1996 | Chappell | ............ | A61F 13/15707 428/152 |
| 5,665,452 A * | 9/1997 | Langdon | ............ | A61F 13/15731 428/131 |
| 5,677,028 A | 10/1997 | Ravella | | |
| 5,693,169 A * | 12/1997 | Langdon | ............ | A61F 13/15731 156/252 |
| H1732 H * | 6/1998 | Johnson | ........................ | 428/131 |
| H1746 H * | 8/1998 | Carrier | .................... | 604/385.23 |
| 5,851,204 A * | 12/1998 | Mizutani | ............ | A61F 13/4753 604/385.04 |
| 5,879,487 A | 3/1999 | Ravella | | |
| 5,899,895 A * | 5/1999 | Robles | ............ | A61F 13/49012 604/385.29 |
| 6,117,523 A * | 9/2000 | Sugahara | .......... | A61F 13/51121 428/134 |
| 6,120,487 A * | 9/2000 | Ashton | ............ | A61F 13/49009 604/358 |
| 6,174,303 B1 | 1/2001 | Suprise et al. | | |
| 6,231,554 B1 * | 5/2001 | Menard | ............... | A61F 13/4752 604/385.01 |
| 6,240,569 B1 * | 6/2001 | Van Gompel | ......... | A61F 13/496 2/400 |
| 6,355,330 B1 * | 3/2002 | Koslow | ............ | A61F 13/15658 428/114 |
| 6,381,994 B1 | 5/2002 | Lee | | |
| 6,610,901 B2 | 8/2003 | McMahon-Ayerst et al. | | |
| 6,861,520 B1 * | 3/2005 | Todd | ................... | C08B 37/0012 424/439 |
| 7,008,887 B2 | 3/2006 | Rearick et al. | | |
| 7,083,604 B2 * | 8/2006 | Sakaguchi | ........ | A61F 13/49011 604/385.24 |
| 7,156,828 B2 * | 1/2007 | Ostrow | ............... | A61F 13/4751 604/369 |
| RE39,919 E * | 11/2007 | Dodge, II | ......... | A61F 13/15203 428/212 |
| 7,322,966 B1 * | 1/2008 | Deerin | .................. | A61F 13/505 604/385.14 |
| 7,951,128 B1 | 5/2011 | Lewis | | |
| 8,117,675 B2 | 2/2012 | Strange et al. | | |
| 2003/0004488 A1 * | 1/2003 | Ashton | ............ | A61F 13/49017 604/385.25 |
| 2003/0124927 A1 * | 7/2003 | Waldroup | .......... | A61F 13/51104 442/50 |
| 2003/0143376 A1 * | 7/2003 | Toyoshima | ....... | A61F 13/51104 428/156 |
| 2004/0229008 A1 * | 11/2004 | Hoying | ............ | A61F 13/15707 428/92 |
| 2004/0265533 A1 * | 12/2004 | Hoying | ............ | A61F 13/15707 428/92 |
| 2005/0055002 A1 | 3/2005 | Whitelaw et al. | | |
| 2005/0131365 A1 * | 6/2005 | Sakaguchi | ........ | A61F 13/49011 604/367 |
| 2008/0108962 A1 * | 5/2008 | Furuta | ............... | A61F 13/15731 604/367 |
| 2008/0275415 A1 | 11/2008 | Wheeler et al. | | |
| 2009/0240224 A1 * | 9/2009 | Underhill | ................ | A61F 13/42 604/367 |
| 2009/0247977 A1 * | 10/2009 | Takeuchi | ............... | A61F 13/511 604/375 |
| 2010/0222759 A1 * | 9/2010 | Hammons | ........... | A61F 13/8405 604/367 |
| 2010/0249736 A1 | 9/2010 | Png et al. | | |
| 2011/0048077 A1 * | 3/2011 | Warren | .................. | A41B 9/001 66/176 |
| 2013/0072888 A1 | 3/2013 | Zorin | | |
| 2014/0039432 A1 | 2/2014 | Dunbar et al. | | |
| 2014/0378935 A1 | 12/2014 | Arayama et al. | | |
| 2016/0089276 A1 * | 3/2016 | Griffiths | ............... | A61F 13/8405 604/360 |

FOREIGN PATENT DOCUMENTS

| | | | |
|---|---|---|---|
| CA | 2152135 | | 12/1995 |
| KR | 10-0694187 | * | 2/2007 |

* cited by examiner

ABSORBENT GARMENT

CROSS REFERENCE TO RELATED APPLICATION

This application is a continuation of U.S. patent application Ser. No. 14/888,435 filed on May 2, 2014, which claims priority under 35 U.S.C. 119(e) from U.S. Provisional Patent Application Ser. No. 61/819,527 filed on May 3, 2013, the contents of which are incorporated herein by reference in their entirety.

FIELD OF THE INVENTION

This following relates generally to garments and more particularly to undergarments with features suitable for dealing with leakages such as stress incontinence.

BACKGROUND OF THE INVENTION

Stress incontinence is a very common condition that involves losing urine unintentionally during physical activity such as exercise, coughing, sneezing or laughing. It is women primarily that experience stress incontinence, often as a result of weaknesses that have been caused in bladder-supporting muscles during childbirth, or as a result of menopause, injury, surgery, or obesity. Despite being very common, women who suffer from stress incontinence or excess fluid release often feel ashamed or embarrassed to be seen wearing or buying the bulky disposable products available in the market.

In the female urinary system, the bladder stores urine produced by kidneys, and is contracted to push out the urine when it is convenient and socially acceptable to do so. There is a sphincter muscle surrounding the bladder neck at the bladder exit, where the bladder neck connects to urethra for conveying the urine outside of the body. The urethra extends from the bladder neck to an outlet located near the cervix in the vagina.

The condition of the pelvic floor muscles, located at the base of the pelvis, has much to do with urinary incontinence. The pelvic organs (the bladder, the vagina, the uterus and the rectum) are supported by a complex "hammock" that includes different types of muscles and tissues. The pelvic floor muscles help to support the sphincter muscle that keeps the bladder closed while it fills with urine.

The female urethra is composed of four (4) separate tissue layers that keep it closed. The inner mucosal lining keeps the urothelium moist and the urethra supple. The vascular spongy coat produces the mucus important in the mucosal seal mechanism. Compression from the middle muscular coat helps to maintain the resting urethral closure mechanism. The outer seromuscular layer augments the closure pressure provided by the muscular layer.

Fast-twitch fibers in these muscles cause the sudden stopping of the urinary stream to provide the voluntary guarding reflex. With acute increases in intra-abdominal pressure, forceful contraction of the fast-twitch levator fibers elevates the pelvic floor and tightens intact connective tissue planes, thereby supporting the pelvic viscera.

Deficiency in the hammocklike support of the endopelvic connective tissue, coupled with relative preservation of the preferentially anterior urethral support of the pubourethral ligaments, may partially explain the complex rotational and descending motion of the bladder neck commonly observed in association with stress incontinence. The pubourethral ligaments may serve to limit downward motion of the anterior urethral wall and provide a pivot point for rotatory motion around the pubic bone. Some theorize that this preferential anterior wall support also may serve to pull the anterior and posterior urethral walls apart during straining, thereby contributing to bladder neck incompetency and stress incontinence.

Unlike in males, where the bladder neck and the prostate comprise the internal urinary sphincter, the internal sphincter in females is functional rather than anatomic. The bladder neck and proximal urethra constitute the female internal sphincter. The female external sphincter (i.e., the rhabdosphincter) has the most prominent effect on the female urethra at the urogenital triangle. Located approximately 1.8 cm distal to the bladder neck, it exerts influence for a distance of approximately 1.5 cm of urethral length.

The female urethra contains an internal sphincter and an external sphincter. The internal sphincter is more of a functional concept than a distinct anatomic entity. The external sphincter is the muscle that is known to be strengthened by Kegel exercises.

While there are numerous physical/muscular conditions that can interfere with the normal functioning of the bladder and the sphincter leading to incontinence, there can be neurological causes also. For example, signals sent from the bladder to the brain may be interfered with due to nerve damage caused by diseases such as diabetes, Parkinson's disease, multiple sclerosis, or strokes due to high blood pressure, leading to incontinence resulting from signal miscommunications.

Products are known for dealing with leakages such as menstruation. However, there are differences between the physical attributes of such leakages and those of stress incontinence, including fluid pressure and volume per emission. Furthermore, the placement of the urethra is further forward in the vagina than where menstruation fluids are excreted. Involuntarily leakages during stress incontinence come from the urethra which is composed of 4 different tissue layers that keep it closed. Fast-twitch fibres in these muscles cause the sudden stopping of the urinary stream to provide the voluntary guarding reflex. It is the weakening of these muscles that causes stress incontinence. However, the muscles often retain some retracting capabilities, and this prohibits women from excreting the full contents in their bladder.

It has been observed that, when urine is released from the urethra as the result of stress incontinence, it is released in spurts directed generally at the same position and angle each time. A stress incontinence product is required to perform differently than a general "leakage product" i.e. more specifically, it is required to perform differently than a product designed solely for menstruation. Furthermore, women often prefer garments that will contact their skin with natural fibres, such as cotton.

Various absorbent articles and protective garments are known. For example, U.S. Pat. Nos. 5,677,028 and 5,879,487 to Ravella each disclose an absorbent material and method for making same comprising a fibre web, including a fibre blend comprising from about 50 to about 75 weight percent of a fibre having fineness less than about 3 denier and from about 25 to about 50 weight percent of a fibre having fineness ranging from about 3 to about 5 denier wherein the fibre web is bound together by fibre bundles transverse to the plane of the web. The fibre blend may further comprise from about 3 to about 7 percent by weight of a fibre having fineness greater than about 5 denier. The fibres comprising the fibre blend may be entirely hydrophobic, or the about 3 to about 5 denier fibre may be hydrophilic.

The absorbent material exhibits a high degree of absorption and fluid retention and does not wet back even under compression. The transverse fibre bundles formed during the mechanical bonding of the web function as wicks for transferring fluid from the surface of the material to the inner portion of the material. The fibre bundles also act as support structures resisting compression and maintaining void space and absorbent surface area within the material, even when wet. The material is reusable and is strong enough to withstand numerous washings. The material is useful as a component of reusable absorbent products further comprising an outer layer or body-side layer. The outer layer may be fluid impermeable, gas permeable or both.

Canadian Patent Application No. 2,152,135 to Ravella discloses a breathable absorbent pad having a fluid impermeable and gas permeable bottom layer and a moisture absorbent layer disposed on said bottom layer. In an embodiment, the absorbent pad may further comprise a fluid permeable top layer wherein the absorbent material is disposed between the top layer and the bottom layer. According to the patent application, high density stitching unexpectedly improves the absorbency of a graduated density non-woven material usable as the moisture absorbent layer with or without the top layer. The application also discloses a method of making a breathable absorbent pad comprising the steps of providing a fluid impermeable and gas permeable bottom layer, a moisture absorbent layer and securing the layers together. Stitching of the top and bottom of a binding material through the layers secures the layers together. The method may further comprise the step of providing a top layer and stitching the top layer and the moisture absorbent layer together.

U.S. Pat. No. 6,381,994 to Lee discloses a method for making a woven or knitted fabric with water transition ability, involving the steps of fabricating a woven or knitted fabric having a double weave structure by use of a polyethyleneterephthalate (PET) filament for one surface of said fabric and a divided PET/nylon-conjugated fibre for the other surface of said fabric, and subjecting said fabric to a weight loss finishing process. According to the patent, since the fabric has a void size difference between the surfaces thereof in accordance with the weight loss finishing process, it can externally discharge, at a high velocity, moisture absorbed therein.

U.S. Pat. No. 8,117,675 to Strange et al. discloses a waterproof panty with rolled over welded seams. According to the patent, the rolled over welded seam will inhibit the leaking of bodily fluids at the leg openings caused by stitching and wicking. The panty has an outer shell and an inner panty layer. The outer shell a continuous cut formed of a soft blend laminated fabric. It is liquid proof, breathable, hypo-allergenic, stain resistant, and elastic. It is cut to form a waist opening and two leg openings. If desired stretchable lace or elastic side portions can be provided. The inner panty lining is a breathable soft blend fabric and includes a front portion, back portion and a crotch portion. The crotch portion is double layered for added dryness. The inner panty layer is cut to the full design of the panty having a waist opening and two leg openings.

U.S. Pat. No. 6,610,901 to McMahon-Ayerst et al. discloses a protective garment, which may be in the form of an undergarment or outerwear, such as a swimwear. The garment includes a body conforming portion for preventing leakage of body waste liquids. The garment includes, at least in the area of the garment which might come into contact with the body waste liquids, sheet material which comprises a lamination consisting of only two laminae. The first lamina is a liquid permeable fabric and the second lamina is a liquid impermeable but vapor permeable material. The liquid permeable fabric is positioned interiorly of the liquid impermeable but vapor permeable material having regard to the inside and outside of such a garment. Liquids are permitted to pass into and through the inner liquid permeable lamina to the interface between the inner laminae and liquid impermeable outer laminae whereat this liquid can be evaporated or dehydrated through the vapor permeable outer laminae.

U.S. Pat. No. 7,951,128 to Lewis discloses a protective undergarment system for absorbing fluids released by the body of a user. The protective undergarment system includes an upper member being designed for being selectively positioned around an abdomen, a groin and a posterior of the user. The upper member comprises a lower aperture extending through the upper member whereby the lower aperture is designed for extending from a portion of the groin to a portion of the posterior and passes between the legs of the user. A lower member is selectively coupled to the upper member whereby the lower member is selectively positioned over the lower aperture of the upper member to selectively close the lower aperture of the upper member. The lower member is designed for absorbing the fluids released by the body whereby the lower member can be removed from the lower member when the lower member is soiled.

U.S. Pat. No. 6,861,520 to Todd et al. discloses a process for chemically bonding an odor-encapsulating agent to textiles includes reacting a cyclodextrin with a cross-linking agent capable of forming ether bonds with the cyclodextrin and with the textile material, and curing the textile material treated with a mixture of the cyclodextrin and cross-linking agent. Preferably, the cross-linking agent is imidazolidone, which forms an ether bond with a hydroxyl group on the cyclodextrin and with a hydroxyl group. In textile materials containing cellulose, imidazolidone forms an ether bond with a hydroxyl group on the cellulose. An active agent can be complexed with the cyclodextrin for release. Textiles formed by such a process can comprise an article of clothing adapted to trap odors emanating from a wearer.

U.S. Patent Application Publication No. 2010/0249736 to PNG et al. discloses protective garments comprising an inner surface or portion of an inner surface with both absorbent and stain resistant properties while maintaining the soft feel, breathability and aesthetic properties associated with traditional "non protective" intimate apparel. The fabrics and methods of constructing the garments are also disclosed.

Korean Patent Registration No. 10-0694187 to Lee discloses an absorbent pad including a water preserving layer having functions of absorbing and storing moisture, a waterproof layer for preventing permeation of the moisture, and a water repellent treatment portion formed along an edge portion of the water preserving layer. The absorbent pad is provided to prevent excessive absorbed urine or moisture from being penetrated into side portions of the pad by only storing the user's urine or moisture on the center portion of an absorbing layer. This is provided to prevent cloth from being wet due to leakage of water thereby providing sanitary and clean environment.

U.S. Pat. No. 7,008,887 to Rearick et al. discloses cellulosic substrates with reduced absorbent capacity having the capability to wick liquids, as well as to methods of manufacturing such cellulosic substrates. The cellulosic substrates provided comprise an inside and an outside connected to the inside. The inside comprises cellulosic fibres and has a reduced absorbent capacity, and the outside comprises cellulosic fibres. The outside may have a reduced absorbent capacity and may have an absorbent capacity higher than the inside. The cellulosic substrate is capable of wicking liquid contacting the inside of the substrate to the outside of the substrate.

While various combinations of materials and layers for absorbent articles are known, improvements are desirable for providing a highly-functional absorbent product suitable for dealing with stress incontinence while also being discrete, comfortable and desirable to wear.

SUMMARY OF THE INVENTION

In accordance with an aspect, there is provided an undergarment comprising a body portion having an upper edge defining a waistband, two leg openings and a crotch region between the leg openings; an absorbent pad on the inside of the body portion within at least the crotch region, the absorbent pad having an inner region and a peripheral region; and elastic bonding film bonded to each of the two leg openings and overlying respective portions of the peripheral region of the absorbent pad thereby to seamlessly bond the absorbent pad with the body portion.

In an embodiment, a wicking layer is overlying the absorbent pad within the crotch region for wicking moisture away from a user of the undergarment towards the absorbent pad. In one embodiment, the wicking layer comprises cotton. In one embodiment, the elastic bonding film also overlies a peripheral region of the wicking layer thereby to bond the wicking layer, the absorbent pad, and the body portion. In one embodiment, the wicking layer is adapted to spread moisture prior to reaching the absorbent pad thereby to reduce the rate at which the absorbent pad is locally saturated.

In an embodiment, the absorbent pad comprises an absorbent layer and a moisture-barrier layer. In one embodiment, the moisture barrier layer is a moisture-barrier treatment and/or film. In one embodiment, the absorbent layer and the moisture-barrier layer are thermal-compression bonded together around their periphery thereby to form the peripheral region. In one embodiment, the thermal-compression increases the density of the peripheral region thereby to facilitate bonding with the elastic bonding film.

In one embodiment, there is provided a moisture-repellent adjacent to and inside the peripheral region of the absorbent pad, wherein the moisture-repellent resists passage of moisture from within the absorbent pad towards the peripheral region.

In accordance with another aspect, there is provided a method of manufacturing an undergarment comprising arranging an absorbent pad within at least a crotch region between two leg openings of a body portion; and seamlessly bonding the absorbent pad with the body portion by lining the leg openings with elastic bonding film bonded to the leg openings overlying respective portions of a peripheral region of the absorbent pad.

In an embodiment, prior to lining the leg openings with elastic bonding film, a wicking layer is overlaid on the absorbent pad, wherein the elastic bonding film also overlies a peripheral region of the wicking layer thereby to bond the wicking layer, the absorbent pad, and the body portion.

In accordance with yet another aspect there is provided an undergarment comprising a body portion having a crotch region between two leg openings and an absorbent pad seamlessly bonded within the crotch region with the body portion with elastic bonding film that is lining and bonded to the leg openings and overlying a peripheral region of the absorbent pad.

In one embodiment, the undergarment further comprises a wicking layer overlying the absorbent pad, wherein the elastic bonding film also overlies a peripheral region of the wicking layer thereby to bond the wicking layer, the absorbent pad, and the body portion.

The absorbent pad of the undergarment or panty may comprise an antimicrobial fibre such as silver.

The combinations of features disclosed herein are intended to obviate the need for stitching to affix an absorbent pad to a body portion of an undergarment. Such additional stitching can add unseemly bulk to the undergarment that is visible through the undergarment and also through tighter-fitting overgarments such as dresses, yoga pants, and the like. Such bulkiness and visibility reduces the usability and attractiveness of the undergarments. For example, users will not want to wear them unless the overgarments are themselves suitable for hiding the bulk, because particularly underneath tighter clothing, prior art undergarments with moisture-absorbent functionality will appear quite differently than prior art undergarments without the moisture-absorbent functionality. The construction described herein enables formation of a substantially seamless absorbent undergarment that is invisible or very closely comparable in invisibility to known, non-absorbent undergarments, under even tight-fitting clothes.

According to certain embodiments disclosed herein, employing elastic bonding film in combination with the peripheral region that is thinner than an inner region of the absorbent pad as described herein provides an excellent bond with the body portion. The thinner absorbent pad peripheral region having been, in one embodiment, produced due to thermo-compression bonding further has an increased density. This enables a greater surface area of the peripheral region to be in contact with the elastic bonding film which, in turn, produces a more reliable bond with the elastic bonding film than would be the case were the film overlying a non-compressed, less-dense peripheral region.

Furthermore, with the elastic bonding film lining the leg openings and continuing on to overlie respective portions of the peripheral regions, an increase in the structural unity of the absorbent pad and the body portion may be observed. As a result, the absorbent pad is more likely to remain in a suitable position for absorbing moisture as intended during activities such as walking, exercising, and the like. As a result, users will be comfortable and the moisture-absorbency capabilities of the absorbent pad can remained properly positioned for effective use.

Advantageously, configurations described herein enable provision of physically-stable moisture-absorbent undergarments that are substantially seamless. Such configurations enable these functional undergarments to be comfortable and entirely aesthetically compatible with tight-fitting clothing such that they do not obviously betray that they are capable of moisture absorption.

BRIEF DESCRIPTION OF THE DRAWINGS

Embodiments of the invention will now be described with reference to the appended drawings in which.

DETAILED DESCRIPTION

Figure 1:
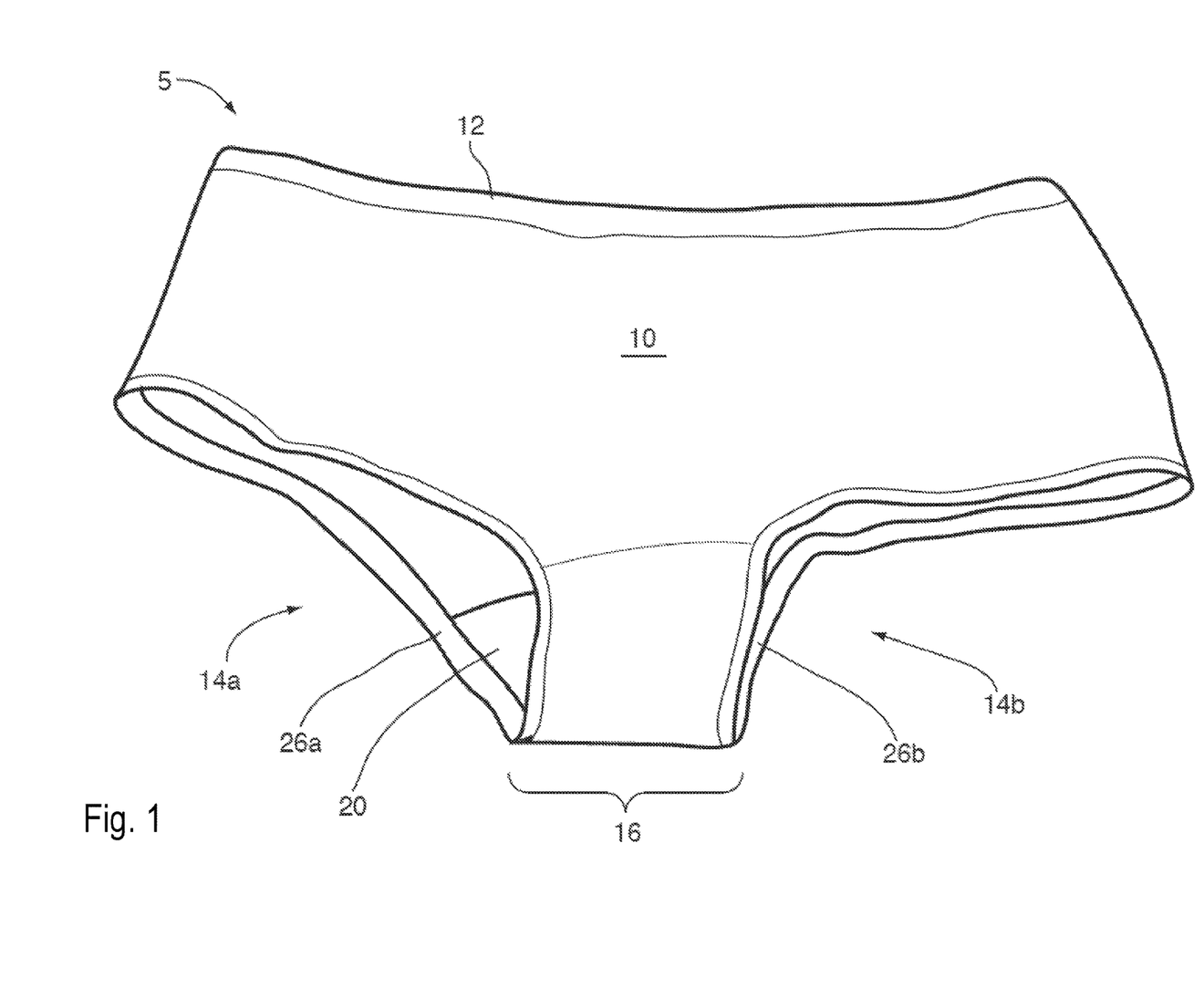
FIG. 1 is an elevation view of the front of an absorbent undergarment according to an embodiment.

FIG. 1 is an elevation view of the front of an absorbent undergarment 5, in this embodiment a panty. Absorbent undergarment 5 includes a body portion 10 having an upper edge 12 defining a waistband, two leg openings 14a and 14b and a crotch region 16 between the leg openings 14a, 14b. An absorbent pad 20 is on the inside of the body portion 10 within at least the crotch region 16.

Figure 2:
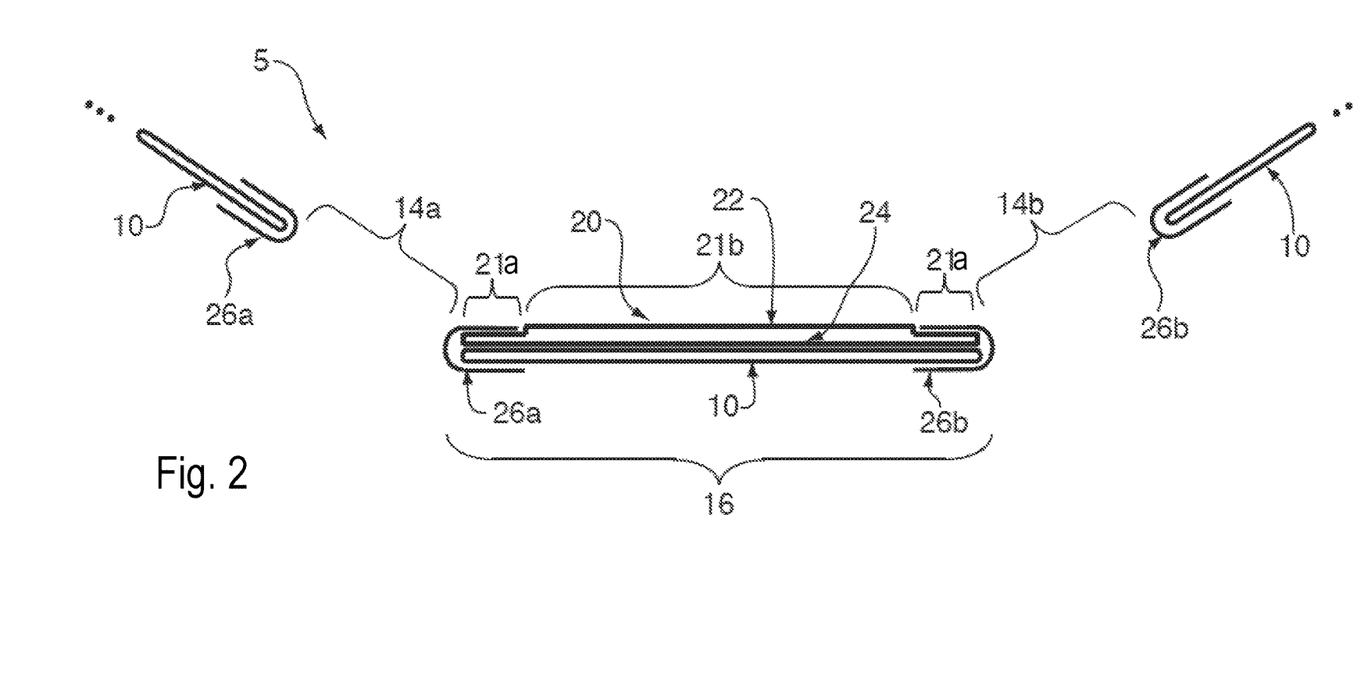
FIG. 2 is a cross-sectional view of a portion of the absorbent undergarment of FIG. 1.

FIG. 2 is a cross-sectional view of a portion of the absorbent undergarment 5. Absorbent pad 20 includes a peripheral region 21a and an inner region 21b. The peripheral region 21a is a generally uniform-width strip running the periphery of the absorbent pad 20, and encloses the inner region 21b. As will be described, the overall thickness of the absorbent pad 20 through the inner region 21b is quite small. Furthermore, the overall thickness of the absorbent pad 20 in the peripheral region 21a is less than that of the inner region 21b, as it has been reduced in thickness as will be described. Strips of thin elastic bonding film 26a and 26b line respective leg openings 14a, 14b and overlie respective portions of the peripheral region 21a of the absorbent pad 20 thereby to bond with the absorbent pad 20 and the body portion 10 so as to structurally unite the respective elastic bonding films 26a, 26b, the absorbent pad 20, and the body portion 10.

In this embodiment, the thickness of each of the strips of elastic bonding film 26a and 26b is about equal to the difference in thickness between the peripheral region 21a and the inner region 21b of the absorbent pad 20. As such, when the portions are pressed together the elastic bonding film 26a, 26b comes in generally flush with the top of the inner region 21b, providing a uniform thickness of absorbent undergarment 5 extending from the leg openings 14a, 14b through to the inner region 21b. This construction enables undergarment 5 to be very smooth and seam-free, such that it is comfortable for the wearer and aesthetically compatible with tight-fitting clothing.

In alternative embodiments, the strips of elastic bonding film 26a, 26b may just slightly overlap the inner region 21b, or alternatively be just slightly spaced from the interface between the peripheral region 21a and the inner region 21b.

On the other side of leg openings 14a and 14b the strips of elastic bonding film 26a and 26b are bonded just to the body portion 10. In this embodiment the absorbent pad 20 does not extend outside of the crotch region 16. For ease of understanding, the strips of elastic bonding film 26a and 26b in FIG. 2 are shown slightly separated from the absorbent pad 20, and the absorbent pad is shown slightly separated from the body 10 of the undergarment 5. However, the layers described above have been pressed together once the undergarment 5 is assembled and ready for use.

In this embodiment, the absorbent pad 20 is similar to configurations disclosed in Korean Patent Registration No. 10-0694187 to Lee, the contents of which are incorporated herein by reference in their entirety. The undergarment 5 incorporating such an absorbent pad 20 may be washed and re-worn numerous times. In this embodiment, the absorbent pad 20 comprises an absorbent layer 22 and a barrier film layer 24. During construction/assembly of undergarment 5, the barrier film layer 24 is oriented so as to be positioned between the absorbent layer 22 and the body portion 10 of the absorbent undergarment 5. The absorbent layer 22, in this embodiment, comprises silver antimicrobial fibre for odour and microbial control. Other varieties of antimicrobial fibres may be employed for this purpose. The reduced-thickness peripheral region 21a of the absorbent pad 20 is formed by thermo-compression bonding the barrier film layer 24 and the absorbent layer 22 together along their respective peripheries, which serves to both structurally unite the barrier film layer 24 and the absorbent layer 22 and also to reduce the overall thickness of the absorbent pad 20 in this peripheral region 21a, as compared with the inner region 21b. Furthermore, the thermo-compression provides a denser, more uniform surface against which the strips of elastic bonding film 26a and 26b can be reliably bonded. The relatively high density of the peripheral region 21a is also believed to help to hinder any wicking of moisture through the peripheral region 21a.

In this embodiment, the reduced-thickness peripheral region 21a is immediately adjacent to the edges of the absorbent pad 20, but in other embodiments the reduced thickness peripheral region 21a may be spaced slightly inwardly from the edges of the absorbent pad 20.

Figure 3:
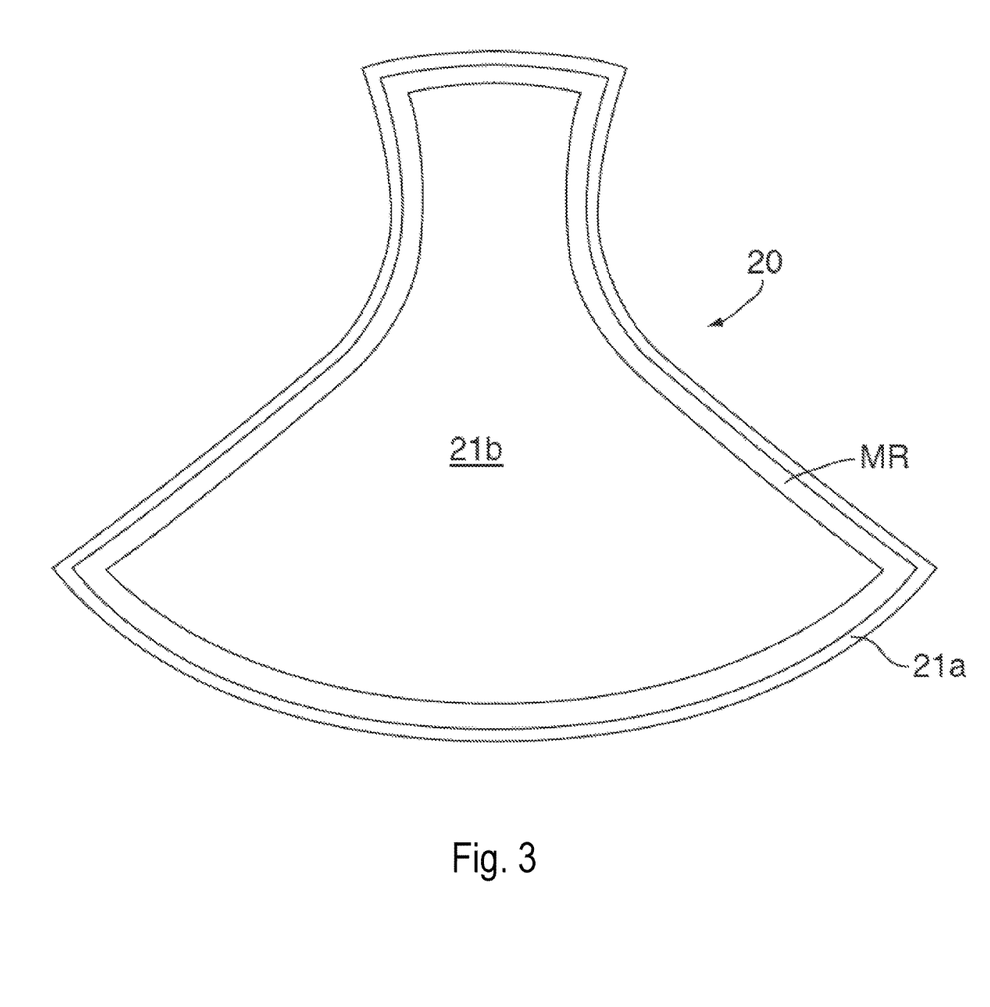
FIG. 3 is a top view of the absorbent pad of the absorbent undergarment of FIG. 1, in isolation.

FIG. 3 is a top view of the absorbent pad 20 of the absorbent undergarment 5, in isolation. The reduced-thickness peripheral region 21a can be seen as a thin strip running along the periphery of the absorbent pad 20. Furthermore, a moisture-repellent strip MR runs along the inside of the peripheral region 21a within the inner region 21b. The moisture-repellent strip MR serves to inhibit passage of moisture that may enter into, and migrate outwards from, the inner region 21b towards the peripheral region 21a. This further inhibits leakage of moisture outside of the absorbent pad 20.

Figure 4:
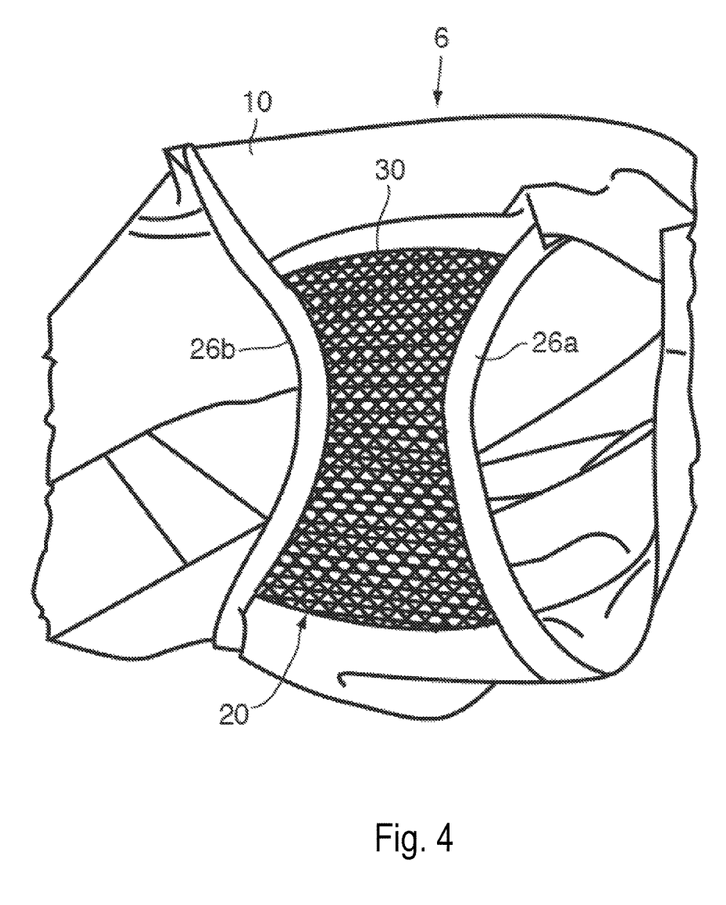
FIG. 4 is a top view of an absorbent undergarment according to an alternative embodiment.

FIG. 4 is a top view of a portion of an absorbent undergarment 6, according to an alternative embodiment. Undergarment 6 is very similar to undergarment 5 with the exception that undergarment 6 includes an additional wicking layer 30 overlying the absorbent pad 20 within the crotch region 16 for wicking moisture away from a user of the undergarment 6 towards the absorbent pad 20. It can be seen in FIG. 4 that elastic bonding film 26a, 26b is not positioned at the front and back of the wicking layer 30 and the absorbent pad 20. Because each of these areas will be at the top of inclines with respect to the exit area of spurts of urine, it is unlikely that such spurts will reach and go past these areas without already having been suitably absorbed into the wicking layer 30 and the absorbent pad 20. As such, provided the absorbent pad 20 extends suitable frontwards and backwards, elastic bonding film 26a, 26b is not required along these front and back positions to help block migration of moisture in frontwards and backwards directions.

Figure 5:
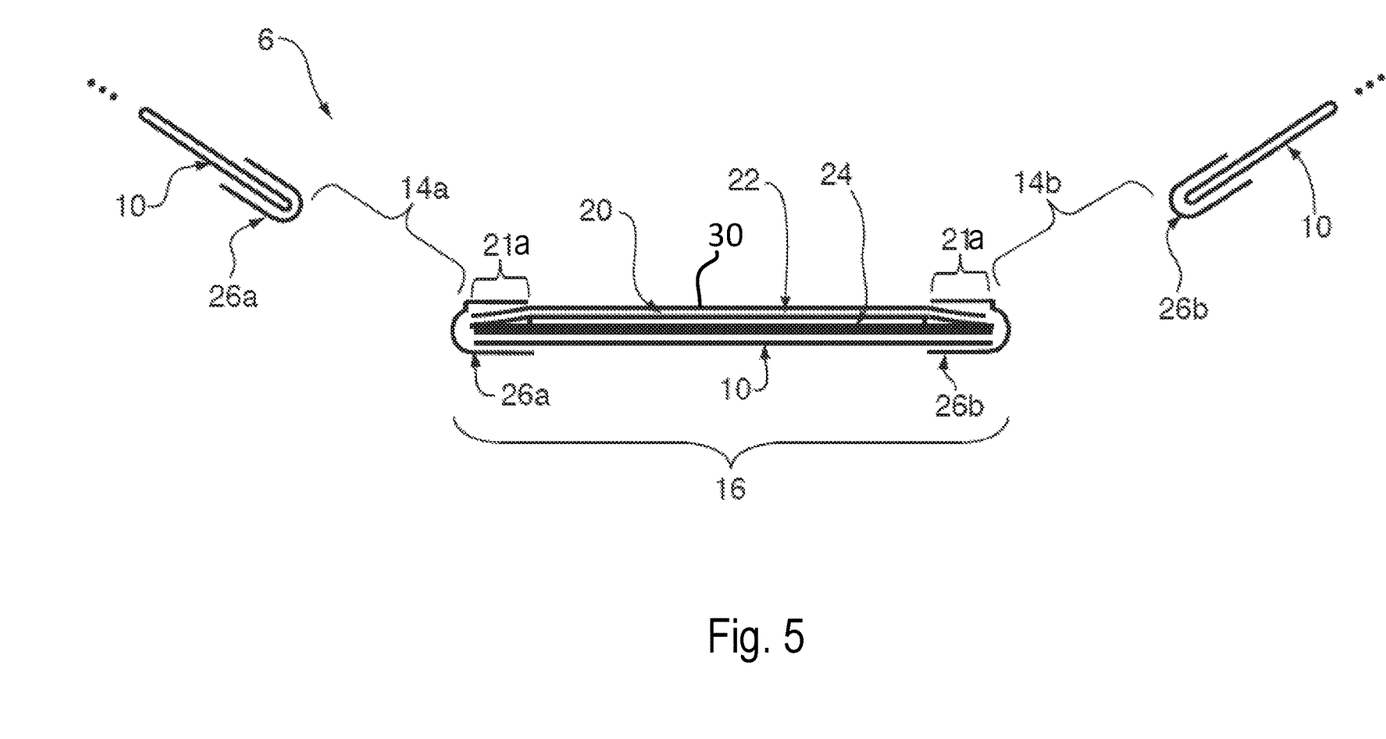
FIG. 5 is a cross-sectional view of a portion of the absorbent undergarment of FIG. 4.

FIG. 5 is a cross-sectional view of a portion of absorbent undergarment 6. As shown, the strips of elastic bonding film 26a and 26b also overlie the additional wicking layer 30 so as to bond and thereby structurally unite the wicking layer 30, the absorbent pad 20, and the body portion 10.

While absorbent pad 20 already has wicking features that provide absorption of moisture, the additional wicking layer 30 provides further wicking and also serves to spread moisture that has entered into the wicking layer 30 from the direction of a user of the undergarment 6, prior to reaching the absorbent pad 20. This advantageously reduces the rate at which the absorbent pad 20 is locally saturated. As described above, spurts of urine occurring during stress incontinence can be incident on a particular central portion of the absorbent pad 20. With the additional wicking through the wicking layer 30 towards the absorbent pad 20, moisture is also wicked by the wicking layer 30 outwards such that the volume of fluid is spread out somewhat and can be received in a wider area of the underlying absorbent pad 20. Thus, the wicking layer 30 and the absorbent pad 20 together provide additional benefits.

The wicking layer 30 may be made of a material such as that described in U.S. Pat. No. 7,008,887 to Rearick et al., the contents of which are incorporated herein by reference in their entirety. Preferably the wicking layer is made of cotton, as cotton is a very comfortable and familiar material for undergarments.

Figure 6A:
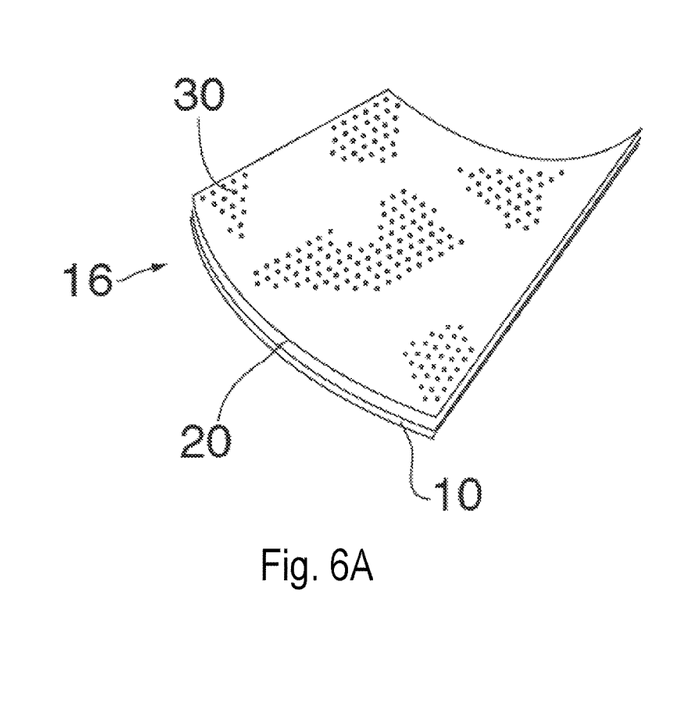
FIG. 6A is a side perspective view of the adjacent layers of a portion of the absorbent undergarment of FIG. 4.
Figure 6B:
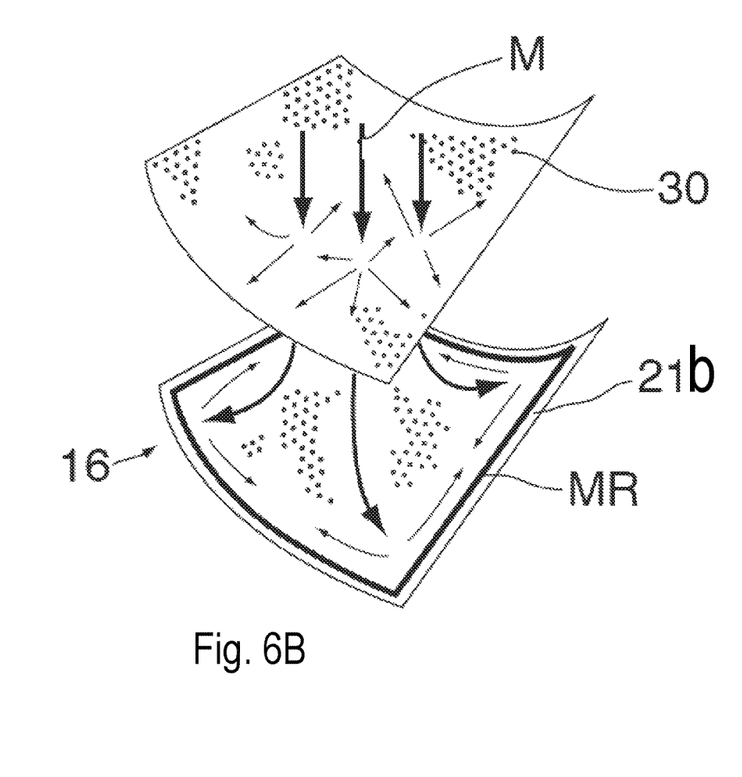
FIG. 6B is a side perspective view of two of the adjacent layers of FIG. 6A, in expanded form.

FIG. 6A is a side perspective view showing a portion of the wicking layer 30 overlying a portion of the absorbent pad 20, which is in turn overlying a portion of the body 10 of undergarment 6. FIG. 6B is a side perspective view of just the wicking layer 30 and the absorbent pad 20, in expanded form. The flow of moisture M entering into wicking layer 30 from a user of the undergarment 6 is shown using arrows. It can be seen that the moisture M entering into wicking layer 30 passes through wicking layer 30 but, in doing so, spreads outwards such that as it enters into absorbent pad 20 it has a larger front. As a result, local saturation of the absorbent pad 20 is slowed. Furthermore, once moisture M has entered into absorbent pad 20, it may eventually migrate towards the peripheral region 21a. However, the strip of moisture repellent MR lining the inside of the peripheral region 21a, in combination with the increased-density peripheral region 21a, not only resists passage of moisture M to outside of absorbent pad 20, but also causes moisture M lining the inside of peripheral region 21a to move generally alongside peripheral region 21a. This further serves to spread the volume of fluid in the absorbent pad 20 to slow the rate of local saturation of the absorbent pad 20.

It has further been found that the strips of elastic bonding film 26a and 26b act as somewhat of a first line of moisture defence for spurts of urine that are incident on the wicking layer 30 but not yet wicked away from the user's skin by the wicking layer 30. This added defence against moisture leaking to overgarments causing stains provides a benefit that is not available from stitched constructions. For example, stitching requires that the materials being connected be punctured, creating potential leakage points.

It has been also discovered that, because of the absorbency, wicking, and directing of moisture along the peripheral region 21a rather than across it, the absorbent pad can be reduced in size compared to prior art absorbent pads. This further contributes to discreteness and comfort for the user.

Although embodiments have been described with reference to the drawings, those of skill in the art will appreciate that variations and modifications may be made without departing from the spirit and scope thereof as defined by the appended claims.

What is claimed is:

1. An undergarment comprising:
    a body portion that includes:
        an upper edge defining a waistband;
        two leg opening regions defining respective leg openings; and
        a crotch region between the leg opening regions;
    an absorbent assembly; and
    strips of elastic bonding film bonding the absorbent assembly to the body portion;
    wherein the absorbent assembly includes:
        an absorbent layer for absorbing moisture received from a wearer of the undergarment; and
        a moisture-barrier layer;
    wherein the absorbent assembly overlies at least the crotch region of the body portion with the moisture-barrier layer facing the body portion and being between the body portion and the absorbent layer;
    wherein the strips of elastic bonding film are bonded to each of the two leg opening regions and bond at least a portion of the absorbent assembly to the body portion; and
    wherein the undergarment is configured to be washed and re-worn numerous times.

2. The undergarment of claim 1, wherein the absorbent assembly further includes a wicking layer overlying the absorbent layer and the crotch region with the absorbent layer being between the moisture-barrier layer and the wicking layer, the wicking layer for wicking moisture away from the wearer of the undergarment towards the absorbent layer.

3. The undergarment of claim 2, wherein each strip of elastic bonding film overlies a respective portion of a peripheral region of the wicking layer.

4. The undergarment of claim 2, wherein the wicking layer is configured to spread moisture prior to reaching the absorbent layer thereby to reduce the rate at which the absorbent layer is locally saturated.

5. The undergarment of claim 2, wherein the wicking layer comprises cotton.

6. The undergarment of claim 1, wherein the moisture-barrier layer includes one or more of a moisture-barrier treatment and a film.

7. The undergarment of claim 1, wherein the absorbent layer and the moisture-barrier layer are thermal-compression bonded together about peripheral region of the absorbent assembly.

8. The undergarment of claim 7, wherein the peripheral region of the absorbent assembly has a higher density than an inner region of the absorbent assembly.

9. The undergarment of claim 1, further comprising a moisture-repellant adjacent to and inside a peripheral region of the absorbent assembly, wherein the moisture-repellant resists passage of moisture from within the absorbent assembly towards the peripheral region of the absorbent assembly.

10. The undergarment of claim 1, wherein the absorbent assembly comprises antimicrobial fibre.

11. The undergarment of claim 10, wherein the antimicrobial fibre comprises silver antimicrobial fibre.

12. The undergarment of claim 1, wherein at least one of the strips of elastic bonding film overlies a respective portion of a peripheral region of the absorbent assembly with the absorbent assembly being between the strip of elastic bonding film and the body portion.

13. The undergarment of claim 1, wherein at least one of the strips of elastic bonding film underlies a respective portion of a peripheral region of the absorbent assembly with the moisture-barrier layer being positioned between the strip of elastic bonding film and the absorbent layer.

14. The undergarment of claim 1, wherein the absorbent assembly is a thermo-compression bonded absorbent assembly.

15. The undergarment of claim 1, wherein the absorbent assembly is seamlessly bonded to the body portion.

16. A method of manufacturing an undergarment having a body portion and an absorbent assembly overlying the body portion, the absorbent assembly having an absorbent layer and a moisture-barrier layer, the method comprising:
    arranging the absorbent assembly over at least a crotch region of the body portion between two leg opening regions of the body portion with the moisture-barrier layer of the absorbent assembly facing the body portion and being between the body portion and the absorbent layer; and bonding the absorbent assembly to the body portion with strips of elastic bonding film positioned within the leg opening;

wherein the undergarment is configured to be washed and re-worn numerous times.

17. The method of claim 16, wherein the absorbent assembly further includes a wicking layer, and wherein the method further comprises, prior to the bonding the absorbent assembly to the body portion, overlying the absorbent layer with the wicking layer with the absorbent layer being between the moisture-barrier layer and the wicking layer.

18. The method of claim 16, wherein the bonding the absorbent assembly to the body portion includes positioning at least one strip of elastic bonding film over a peripheral region of the absorbent assembly with the absorbent assembly being between the strip of elastic bonding film and the body portion to bond at least a portion of the absorbent assembly to the body portion.

19. The method of claim 16, wherein the bonding the absorbent assembly to the body portion includes positioning at least one strip of elastic bonding film under a peripheral region of the absorbent assembly with the moisture-barrier layer between being between the strip of elastic bonding film and the absorbent layer to bond at least a portion of the absorbent assembly to the body portion.

20. The method of claim 16, wherein the absorbent assembly is a thermo-compression bonded absorbent assembly.

21. The method of claim 16, wherein the bonding the absorbent assembly to the body portion includes seamlessly bonding the absorbent assembly to the body portion.

22. A moisture-absorbent panty having a crotch region that comprises:
    an absorbent assembly comprising an absorbent layer overlying a moisture-barrier layer, the absorbent assembly oriented to face a wearer of the moisture-absorbent panty;
    a body layer of the moisture-absorbent panty supporting the absorbent assembly within the crotch region with the moisture-barrier layer being between the body layer and the absorbent layer; and
    strips of elastic bonding film on opposite sides of the crotch region, wherein the strips of elastic bonding film bond at least a portion of the absorbent assembly to the body layer, wherein each strip is:
        bonded to a respective portion of a peripheral region of the absorbent assembly with at least a portion of the absorbent assembly between the body layer and the strip; and
        bonded to the body layer;
    wherein the moisture-absorbent panty is configured to be washed and re-worn numerous times.

23. The moisture-absorbent panty of claim 22, wherein the absorbent assembly further includes a wicking layer overlying the absorbent layer and oriented to face the wearer of the moisture-absorbent panty, wherein at least one of the strips of elastic bonding film is bonded to a respective portion of a peripheral region of the wicking layer with at least a portion of the wicking layer being between the body layer and the strip of elastic bonding film.

24. The moisture-absorbent panty of claim 22, wherein the absorbent assembly is a thermo-compression bonded absorbent assembly.

25. The moisture-absorbent panty of claim 2, wherein the absorbent assembly is seamlessly bonded to the body portion.

* * * * *

UNITED STATES PATENT AND TRADEMARK OFFICE
CERTIFICATE OF CORRECTION

PATENT NO. : 10,441,480 B2
APPLICATION NO. : 15/833248
DATED : October 15, 2019
INVENTOR(S) : Joanna Griffiths Page 1 of 1

It is certified that error appears in the above-identified patent and that said Letters Patent is hereby corrected as shown below:

In the Claims

Claim 7, Column 10, Line 33, insert --a-- after "bonded together about" and before "peripheral region".

Claim 25, Column 12, Line 33, replace "2" with --22--.

Signed and Sealed this
Twenty-eighth Day of January, 2020

Andrei Iancu
*Director of the United States Patent and Trademark Office*